April 25, 1972 D. L. ARMSTRONG Plant Pat. 3,128
ROSE PLANT
Filed May 6, 1970
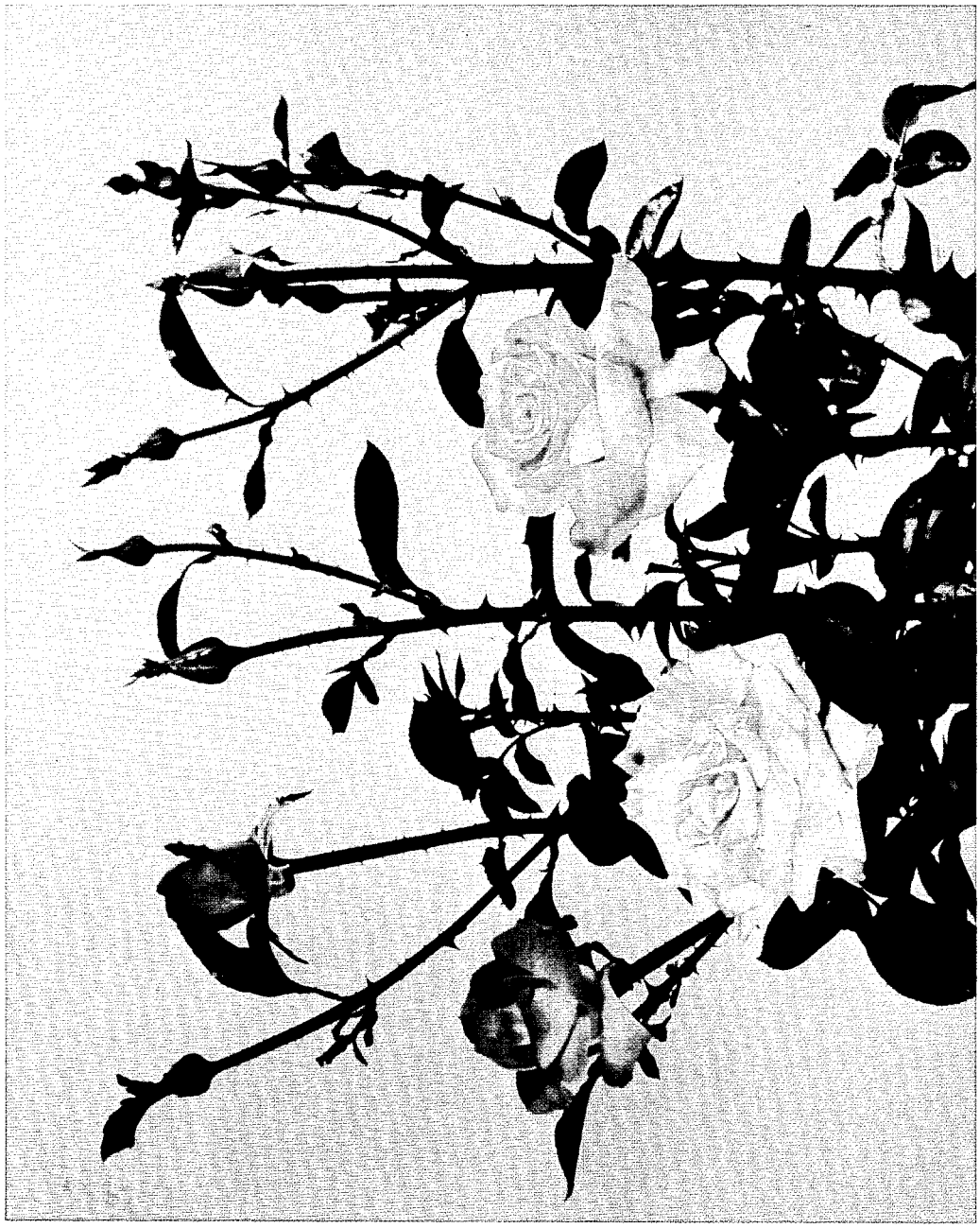

United States Patent Office

Plant Pat. 3,128
Patented Apr. 25, 1972

3,128
ROSE PLANT

David L. Armstrong, Upland, Calif., assignor to
Armstrong Nurseries, Inc., Ontario, Calif.

Filed May 6, 1970, Ser. No. 35,305
Int. Cl. A01h 5/00
U.S. Cl. Plt.—11 1 Claim

ABSTRACT OF THE DISCLOSURE

A grandiflora rose, nearly continuous in bloom during growing season, the plant having above average resistance to mildew and having blooms which retain their freshness for as long as six or seven days on the bush in the garden. The petals of the bloom are precisely imbricated and formally arranged in the flower. The bloom develops a strong purplish pink color. The fragrance is slight. The blooms are average in size and are borne in clusters of from two to four to the stem.

This invention relates to a new variety of grandiflora rose plant, a tall bushy outdoor seedling, cultivated primarily for cut flowers and garden decoration. Its hardiness in diverse climates has not yet been established. The plant holds its distinguishing characteristics through succeeding propagations by budding. It was originally grown in Ontario, Calif.

The accompanying drawing illustrates the plant in color and shows the flowering thereof from bud to full bloom.

Throughout this specification, color names beginning with a small letter signify that the name of that color, as used in common speech, is aptly descriptive. Color names beginning with a capital letter designate values based upon the Nickerson Color Fan, put out by Munsell Color Co.

This new variety was produced by crossing an unnamed seedling, which resulted from Charlotte Armstrong × Contrast, as the seed parent, and another unnamed seedling representing a cross of Fandango × (World's Fair × Floradora), as the pollen parent. The unnamed seed parent was of the hybrid tea class with a large and nearly perfect bud of clear medium pink. The unnamed pollen parent was a bright red of the floribunda class and very vigorous. The present variety is a grandiflora, the flowers of which are of a purplish pink substantially as described and illustrated hereinafter in general color effect.

The present plant is very free and vigorous in growth, in comparison with the seed parent which was not very vigorous. The new variety has somewhat smaller flowers, measuring from 4"–4½" in diameter, whereas the flowers of the seed parent were generally considered rather large, being from 4½"–5" in diameter.

The new variety has not thus far been observed to produce any seed hips, whereas the seed parent develops numerous seed hips in the Ontario, Calif. neighborhood.

This new variety is distinguished from its pollen parent in the following characteristics. The pollen parent is of the floribunda class, whereas this new variety is appropriately classed as a grandiflora. This new variety has blooms of a strong purplish pink color, after three days open, whereas the pollen parent has blooms of a good bright red color.

The new variety is distinguished by its bushy upright and very free vigorous growth, whereas the pollen parent, although vigorous, was quite short.

The flower of the new variety is quite high-centered with beautiful imbrication, whereas the flower of the pollen parent was globular at first and later became quite flat, when fully open.

The foliage of this new variety is of medium size and moderately heavy in texture, whereas the foliage of the pollen parent was quite small and soft.

The flowers of this new variety are usually borne on long strong stems, in irregular clusters, of two to four blooms. The plant blooms very freely outdoors and almost continuously during the growing season. The fragrance of the new blooms is relatively slight, reminiscent of tea roses.

*Bud*

The peduncle is of average length and average caliper, stiff, usually rough with a very few gland-tipped cilia, and numerous prickles. It is a Strong Yellow Green, 5 GY 6/8 in color, overlaid with Deep Purplish Red, 5 RP 3/9 especially where exposed to the sun.

Before the calyx breaks, it is of medium size and medium length, ovoid in form, and generally glabrous, except for a few gland-tipped cilia on the surface of the bud usually with slender, entire, bristle-like foliaceous parts extending beyond the tip of the bud for a distance equal to about one-half or more of its length.

As the calyx breaks, the color is near Strong Purplish Red, 10 RP 4/12. The inner surface of the sepals has a fine wooly tomentum. Margins of alternate sepals are lined with fine wooly tomentum, whereas the margins of the intervening sepals have several small stipitate glands.

As the first petal opens, it is of average size, of medium length, and ovoid in form. Outside, there is a very small area at the base of the petal which is Strong Greenish Yellow, 10 Y 8/11, with definite veins of Light Purplish Pink, 5 RP 8/5, diminishing towards the apex. For the rest of the petal, the color is between Strong Purplish Red, 7.5 RP 4/11 and Strong Purplish Red, 7.5 RP 5/12. Inside, there is a small area at the base which is nearly Vivid Yellow, 5 Y 8/12, changing rapidly to Light Purplish Pink, 5 RP 8/5, which for the outer area of the petal is overlaid with Strong Purplish Red, 10 RP 4/12.

The bud opens up well, and is not prevented from opening by cold, hot, wet, or dry weather.

*Bloom*

When fully open the flowers measure from 4"–4¼" and only occasionally somewhat larger. The petalage is very double, comprising from 40 to 48 petals and 2 to 4 petaloids, which are regularly arranged. The bloom is high-centered at first, becoming flat to high-centered later on.

The petals at first are somewhat cupped with the tips rolled outward. Later, at maturity, they become somewhat loosely cupped with the tips reflexed outward.

The petals are of medium thick and leathery texture. They are slightly velvety on the inside and slightly shiny on the outside. The outside petals are round to slightly obovate in shape, whereas the intermediate and inside petals are obovate.

The paragraphs immediately following describe the color values observed in a flower newly opened in the month of May, on a rose plant which had been grown outdoors in Ontario, Calif. All color values in this application are evaluated from the Nickerson Color Fan, put out by Munsell Color Company, except where the popular, obvious, and ordinary or non-specific terms are used.

The outer surface of the outside petal is between Strong Purplish Red 7.5 RP 4/11, and Deep Purplish Red, 10 RP 3/10, with a very small area at the base of the petal which is nearly white. The inner surface of the outside petal is near Light Purplish Pink, 5 RP 8/5, adjacent the base of the petal. A moderately small area at base is near white. It gradually darkens to a shade between Strong Purplish Pink, 5 RP 7/9, and Deep Purplish Pink, 5 RP 6/10. Towards the apex the color is near Strong Purplish Red, 7.5 RP 4/11.

The outer surface of the intermediate petal has a small area at the base which is Vivid Greenish Yellow, 7.5 Y 8/12, changing rapidly to near white with overtones of Light Purplish Pink, 5 RP 8/5, gradually darkening to Strong Purplish Red, 7.5 RP 5/12, at the apex. The inner surface of the intermediate petal is Vivid Yellow, 5 Y 8/12, in a small area at the base, changing abruptly to near Light Purplish Pink, 5 RP 8/5. This gradually darkens to near Strong Purplish Pink, 5 RP 7/9, but with a sudden flush of Strong Purplish Red, 7.5 RP 4/11, near the apex of the petal.

The outer surface of the inner petal displays a moderately small area at the base which is near Brilliant Yellow, 5 Y 9/9. This gradually blends into a near Deep Purplish Pink, 5 RP 6/10, for the lower half of the petal and into an undiluted Deep Purplish Pink, 5 RP 6/10, for the remainder of the petal. The inner surface of the inside petal has a small area at the base displaying Vivid Greenish Yellow, 7.5 Y 8/12. The remainder of the petal is Light Purplish Pink, 5 RP 8/5, overlaid in some areas with Deep Purplish Pink, 5 RP 6/10.

The paragraphs immediately following describe the color values observed in a bloom which had been open for three days indoors, in the month of May. The plant was grown in Ontario, Calif.

The outer surface of the outside petal was Deep Purplish Pink, 2.5 RP 6/10, overlaid with Strong Purplish Red, 7.5 RP 4/11. A moderate area at the base was nearly white. The inner surface of the outside petal displays a moderate area at the base which is near white, changing rapidly to Light Purplish Pink, 5 RP 8/5, with overlayments of Deep Purplish Pink, 5 RP 6/10, and Moderate Purplish Red, 5 RP 5/10.

The outer surface of the inside petal has a moderate area at the base and a center vein area which is nearly white. The rest of the petal is Light Purplish Pink, 2.5 RP 8/5. The inner surface of the inside petal has a small area at the base which is nearly white and which streaks upward into Strong Purplish Red, 7.5 RP 5/12.

The general color effect of the newly opened flower is between Strong Purplish Red, 7.5 RP 5/12, and Strong Purplish Red, 10 RP 4/12, overlaid onto Strong Purplish Pink, 7.5 RP 7/10.

The bloom which has been open for three days, indoors, gives a general color effect which lies between Strong Purplish Pink, 7.5 RP 6/12, and Strong Purplish Red, 7.5 RP 5/12.

The petals persist, fading to a near white color. They are not affected by cold, hot, wet, or dry weather. On the bush, in the garden, the flowers will persist from 6 to 7 days in September. Cut roses, grown outdoors but kept at living-room temperatures, will last from 4 to 5 days, in the month of September.

*Reproductive organs*

Stamens: The stamens are of average number, regularly arranged about the pistils, a few being mixed with petaloids.

Filaments: The filaments are short, from 3 to 8 mm. long.

Anthers: The anthers are small. They open at various times, and their upper sides are colored Strong Orange Yellow, 10 YR 7/10. The underside is near Strong Orange Yellow, 10 YR 7/10.

Pollen: The pollen is moderate in amount and yellow in color.

Pistils: The pistils may average approximately 36 in number, which may be regarded as ranging from few to average for this type of rose.

Styles: The styles are moderately uneven, short, and very thin. They are somewhat bunched and from 2 to 7 mm. long.

Stigma: The stigma is near Strong Purplish Red, 10 RP 4/12, in color.

Ovaries: The ovaries usually protrude from the calyx, for the most part.

Hips: This variety does not make hips out of doors.

Sepals: The sepals are permanent, and do not display any marked coloration, either inside or out.

Seeds: There are no seeds.

*Foliage*

The compound leaves of the plant comprise usually from 3 to 7 leaflets, and are moderately abundant. They are of medium size, moderately heavy, and semi-glossy in texture. The leaflets range from ovid to lanceolate in shape, with the apex mucronate, the base around, and the margin simply serrate.

The color of the mature leaf on its upper surface is Moderate Yellow Green, 5 GY 5/6, overlaid with a color between Moderate Olive Green, 5 GY 4/3, and Grayish Olive Green, 5 GY 3/2. The undersurface of the mature leaf is Moderate Yellow Green, 5 GY 5/6, between veins, overlaid with white from minute hairs. Veins are Deep Reddish Purple, 2.5 RP 3/8.

The color of the young leaf on the upper surface is Moderate Olive, 5 Y 4/3, overlaid with near Moderate Reddish Brown, 7.5 R 3/6, while the undersurface of the young leaf is near Dark Red, 2.5 R 3/7.

The rachis is of average size, grooved on its upper side with some stipitate glands on the edges. The underside is moderately smooth, with stipitate glands.

The stipules are moderately short and moderately wide, the short points turning out at an angle of less than 45°.

The plant as a whole is more resistant than average to mildew, as compared to other varieties now commercially available and grown under comparable conditions in Ontario, Calif.

*Growth*

The growth habit of the new variety is bushy, upright, and moderately branched. Its growth is very free and vigorous, and its canes are of medium caliper.

The main stems display a color between Strong Yellow Green, 5 GY 6/8, and Moderate Yellow Green, 5 GY 5/6, overlaid with Very Light Yellowish Green, 2.5 G 9/3. The large prickles on the main stems are moderately short, almost straight, with long narrow base. They display a light shading of Dark Greenish Yellow, 7.5 Y 6/7, with a moderate area at the tip which is near Strong Brown, 5 YR 4/5. There are many small prickles, displaying a light shading of Dark Greenish Yellow, 7.5 Y 6/7. There are no hairs.

The coloration of the branches is substantially the same as that of the main stems. The branches carry a few large prickle which, like those on the main stems, are moderately short, almost straight, with moderately long narrow base. The coloration is near Light Olive Brown, 2.5 Y 5/5. There are several small prickles which also are near Light Olive Brown, 2.5 Y 5/5. There are no hairs.

The new shoots are near Strong Yellow Green, 5 GY 6/8, overlaid with areas of Dark Red, 5 R 3/7, where exposed directly to the sun. The large prickles on the new shoots are numerous, moderately short, almost straight, with long base. The color is near Dark Red, 5 R 3/7. There are several small prickles which are near Dark Red, 5 R 3/7, in color. There are no hairs.

I claim:

1. A rose plant of the grandiflora class, substantially as shown and described herein, and being distinguished by combinations of characteristics which include the following features, namely: by free and vigorous habit of growth; by foliage which comprises compound leaves of from three to seven leaflets; by peduncles which are stiff and rough with a few gland-tipping cilia and numerous prickles; by the free blooming and ever blooming habit of the plant; by the orderly arrangement of the precisely-imbricated petals which develop a strong purplish pink color; by the longevity of the blooms which retain their freshness on the bush for as long as six or seven days; and by a resistance to mildew which is above the average.

No references cited.

ROBERT E. BAGWILL, Primary Examiner